United States Patent [19]

Ferro

[11] Patent Number: 5,298,521
[45] Date of Patent: Mar. 29, 1994

[54] 1,5-DIPHENYL-3-PYRAZOLYLALKYL-N-HYDROXYDITHIOCARAMATES, COMPOSITIONS AND USE

[75] Inventor: Michael Ferro, Bridgewater, N.J.

[73] Assignee: Ortho Pharmaceutical Corporation, Raritan, N.J.

[21] Appl. No.: 114,122

[22] Filed: Aug. 30, 1993

[51] Int. Cl.$^5$ .................. A61K 31/415; C07D 231/12
[52] U.S. Cl. .................... 514/406; 514/825; 514/826; 514/863; 548/375.1
[58] Field of Search ...................... 348/375.1; 514/406, 514/825, 826, 863

[56] References Cited

U.S. PATENT DOCUMENTS 5,164,381  11/1992  Wachter et al. ................. 548/375.1

Primary Examiner—Robert W. Ramsuer

[57] ABSTRACT

1,5-Diphenyl-3-pyrazolylalkyl-N-hydroxydithiocarbamates of the general formula:

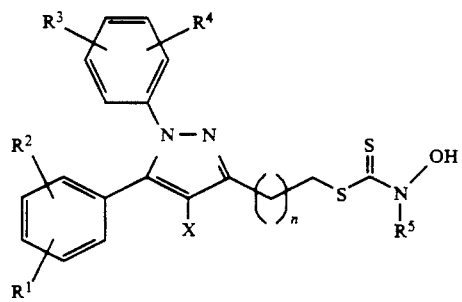

are disclosed to have anti-inflammatory activity in mammals.

11 Claims, No Drawings

1,5-DIPHENYL-3-PYRAZOLYLALKYL-N-HYDROXYDITHIOCARAMATES, COMPOSITIONS AND USE

The present invention relates to substituted pyrazole derivatives, and more particularly, to 1,5-diphenyl-3-pyrazolylalkyl-N-hydroxydithiocarbamates. These compounds are pharmacologically active in alleviating inflammation, asthma, arthritis, hypersensitivity, myocardial ischemia and dermatological conditions, such as, psoriasis and dermatitis, and gastrointestinal inflammatory conditions, such as, inflammatory bowel syndrome.

BACKGROUND OF THE INVENTION

By blocking both cyclooxygenase and 5-lipoxygenase, the two pathways of the arachidonic acid cascade, it is believed that both the acute and chronic stages of inflammatory disease states can be ameliorated.

U.S. Pat. Nos. 4,826,868 and 5,164,381 discloses the anti-inflammatory agent, tepoxalin, which has the structure:

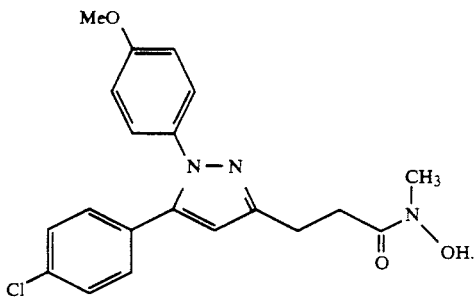

This compound is an effective anti-inflammatory, but further compounds having this utility are desired.

U.S. Pat. No. 5,051,518 discloses anti-inflammatory compounds having the structure:

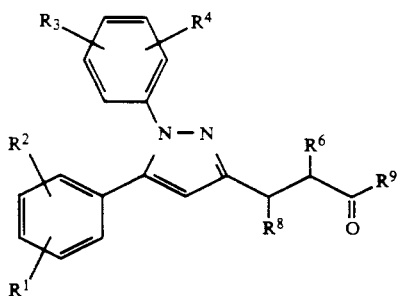

wherein $R^6$ and $R^8$ taken together are part of a ring. These compounds are effective anti-inflammatory agents, but further compounds having this utility are desired.

U.S. Pat. No. 5,242,940 discloses anti-inflammatory compounds having the structure:

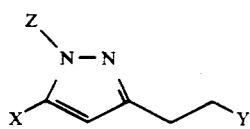

wherein X is certain thienyl, furanyl, and lower alkylpyrrolyl. Again, these compounds are effective anti-inflammatory agents, but further compounds having this utility are desired.

SUMMARY OF THE INVENTION

Briefly, according to the present invention, there are provided anti-inflammatory compounds of the general formula J

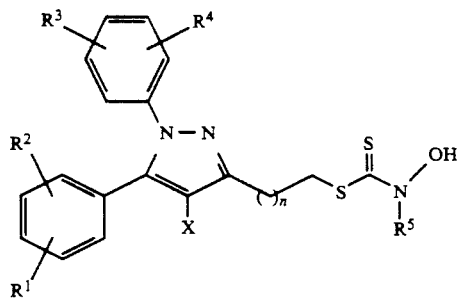

wherein,
- $R^1$ and $R^2$ are independently selected from the group consisting of hydrogen, $C_{1-6}$alkyl, $C_{1-6}$perfluoroalkyl, halogen, $C_{1-6}$alkoxy, $C_{1-6}$alkylsulfinyl, $C_{1-6}$alkylsulfonyl and $C_{1-6}$alkylmercapto;
- $R^3$ and $R^4$ are independently selected from the group consisting of hydrogen, $C_{1-6}$alkyl, halogen, $C_{1-6}$alkoxy, $C_{1-6}$perfluoroalkoxy, $C_{1-6}$alkylsulfinyl, $C_{1-6}$alkylsulfonyl and $C_{1-6}$alkylmercapto;
- $R^5$ is selected from the group consisting of H, $C_{1-6}$alkyl, $C_{1-6}$cycloalkyl and phenyl;
- n is 0, 1 or 2; and
- X is selected from the group consisting of H, Cl, I and Br.

Also provided by the present invention is a method to alleviate inflammation in a mammal exhibiting an inflammatory condition, the method comprising administering to the mammal an effective amount of a pharmaceutical composition containing a unit dose of the substituted pyrazole compound dispersed in a pharmaceutically acceptable carrier.

DETAILED DESCRIPTION OF THE INVENTION

The compounds of the invention can be prepared from the appropriately substituted 3-carboalkoxy-1,5-diaryl pyrazole derivative A, where n=0, 1 or 2. The synthesis of derivative A is illustrated in Schemes 1A to 1C and described below.

Referring to scheme 1A, to prepare derivative A when n=0, an acetophenone, such as, 4'-chloroacetophenone is reacted with a dialkyl oxalate, such as, diethyl oxalate in the manner described in Meister et al., J. Bio. Chem., 1948, 175, 573 to give the 1-phenyl-4-carboalkoxy-1,3-dione derivative B. Derivative B is reacted with an appropriately substituted phenyl hydrazine or its acid addition salt at 0° C. to room temperature for 2-24 h in a suitable inert polar solvent, such as, ethanol to give the desired derivative A.

SCHEME 1A

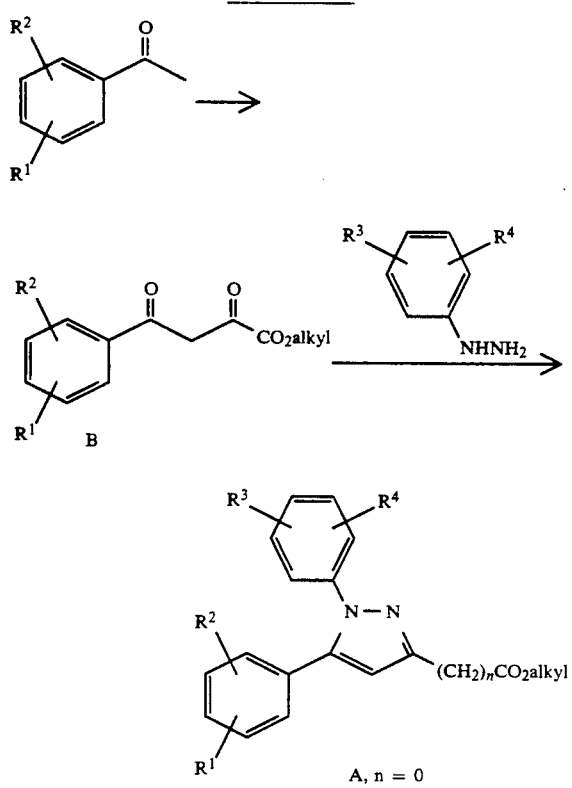

A, n = 0

SCHEME 1B

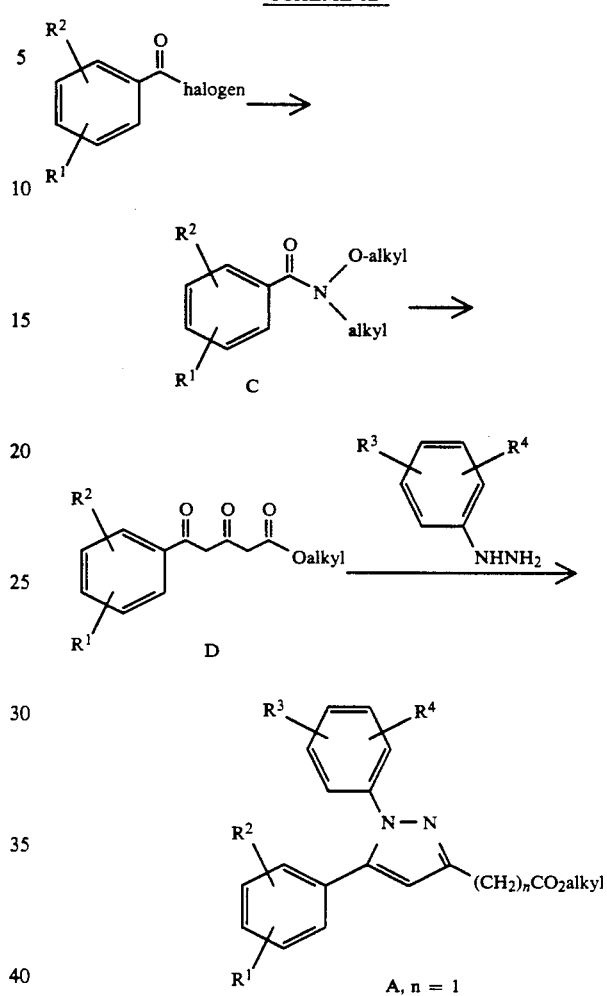

A, n = 1

Referring to Scheme 1B, derivatives A in which n=1, are prepared in a three step reaction. In a first step, an appropriately substituted N,O-dialkylhydroxylamine hydrochloride, such as, N,O-dimethylhydroxylamine hydrochloride is stirred in an inert solvent, such as, methylene chloride with suitable organic base, such as, pyridine under inert atmosphere at 0° C. for 1-2 h. A suitable phenacyl halide derivative, such as, 4'-chlorophenacyl chloride is added and stirred at −5° to 0° C. for 3-12 h. This step gives the desired O-alkyl hydroxamic acid derivative C. In a second step, an alkyl acetoacetate, such as, ethyl acetoacetate is added to an equivalent of an appropriate organic base, such as, NaH, at 0° C. in a suitable solvent, such as, THF for 30 min to 1 h. This mixture is treated with another equivalent of a suitable organic base, such as, n-BuLi, at 0° C. for 30 min to 1 h. The resulting mixture is treated with derivative C at 0° C. to room temperature for 2-16 h to give the 1-phenyl-5-carboalkoxy-1,3-dione derivative D. Alternatively, derivative D may be prepared by treating an alkyl acetoacetate with 2 equivalents of an organic base, such as, LDA or lithium hexamethyldisilazide at −78° C. in an appropriate solvent, such as, THF for 30 min to 1 h followed by treatment with compound C at −78° C. to room temperature for 30 min to 2 h. In a third step, derivative D is reacted with an appropriately substituted phenylhydrazine, such as, phenylhydrazine or its acid addition salt at 0° C. to room temperature for 2-24 h in a suitable inert polar solvent, such as, ethanol to give the desired derivative A.

Referring to Scheme 1C, derivatives A in which n=2, are prepared from known starting materials in a two step reaction. In a first step, 6-phenyl-4,6-diketohexanoic acid derivatives E, such as, 6-(4'-chlorophenyl)-4,6diketohexanoic acid, are treated with an appropriately substituted phenyl hydrazine or its acid addition salts in a suitable inert polar solvent, such as, ethanol at room temperature for 2-24 h to give the desired 1,5-diaryl3-pyrazole propionic acid derivative F. In a subsequent step, treatment of derivative F with $CH_2N_2$ in an inert solvent, such as, $Et_2O$ and $CH_2Cl_2$ at 0° C. to room temperature for 15 min to 1 h gives the desired derivative A. The preparation of the starting material, derivative E, and reaction conditions for Scheme 1C are disclosed in greater detail in U.S. Pat. No. 5,164,381, which is hereby incorporated by reference. Specifically derivative E, may be produced by treating an acetophenone derivative which is appropriately substituted on its phenyl ring with succinic anhydride and an appropriate organic base such as LiHMDS, LDA or NaH in an appropriate solvent such as THF at −78° C. to room temperature for 1-5 hours.

SCHEME 1C

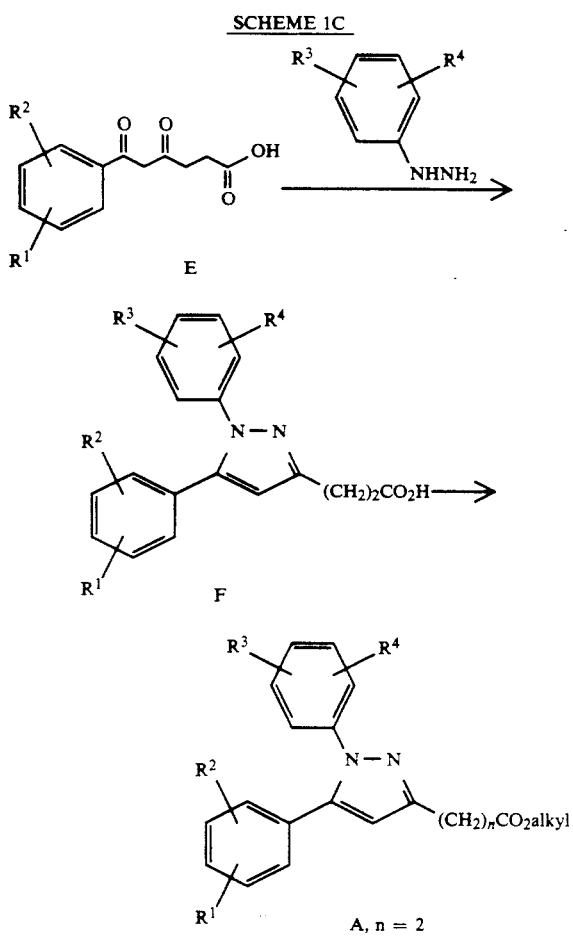

The synthesis, from derivative A, of the compounds of the invention is illustrated in Scheme 2. Referring to Scheme 2, derivative A is treated with a reducing agent, such as, lithium aluminum hydride, in an inert solvent, such as, THF at 0° C. to room temperature for 1-6 h to give desired alcohol derivative G. A variety of reducing agents may be employed which include, sodium borohydride, diisobutylaluminum hydride, lithium borohydride and sodium trimethoxyborohydride coupled with their appropriate solvents. Alternatively, in the case where n=2, derivative G can be synthesized using the methods disclosed in U.S. Pat. No. 5,164,381. Subsequently, derivative G is treated with a halogenating agent, such as, thionyl chloride in an appropriate solvent, such as, pyridine to give the halide derivative H. A variety of halogenating agents may be used to replace thionyl chloride including $PCl_5$, $PBr_3$, LiBr and $Ph_3.I_2$. For the final step, a suitable N-alkylhydroxyl amine, such as, N-methylhydroxylamine and carbon disulfide are combined at room temperature and immediately diluted with triethylamine to produce the reactive alkyl N-hydroxydithiocarbamate salt I. Salt I is then treated with derivative H in a suitable inert solvent such DMF at 60°-100° C. for 30-120 min to give the compounds of the invention.

Scheme 2 may be modified in two variations to produce the compounds of the invention where X=Cl, I or Br. In the first variation, treatment of derivative A with a halogenating agent, such as, N-chlorosuccinimide (NCS) in an inert solvent, such as, methylene chloride at room temperature for 2 to 16 h gives derivative A where X=Cl. Alternative halogenating agents could be substituted for NCS and include NBS, $I_2$, $Cl_2$ and $Br_2$. The 4-halogenated derivative A' is treated in the same manner described above for its unsubstituted counterpart to give, successively, G', H' and the 1,5-diphenyl-3-pyrazolylalkyl-N-hydroxydithiocarbamates of the invention where X=Cl, I or Br.

In the second variation of Scheme 2, the alcohol derivative G is treated with a halogenating agent, such as, N-chlorosuccinimide (NCS) in an inert solvent, such as, methylene chloride at room temperature for 2 to 16 h to give derivative G' where X=Cl. Alternative halogenating agents could be substituted for NCS and include NBS, NIS, $I_2$, $Cl_2$ and $Br_2$. The halogenated derivative G' may be treated in the same manner described above for its unsubstituted counterpart to give, successively, H' and the 1,5-diaryl-3-pyrazolylalkyl-N-hydroxydithiocarbamates of the invention where X=Cl, I or Br.

SCHEME 2

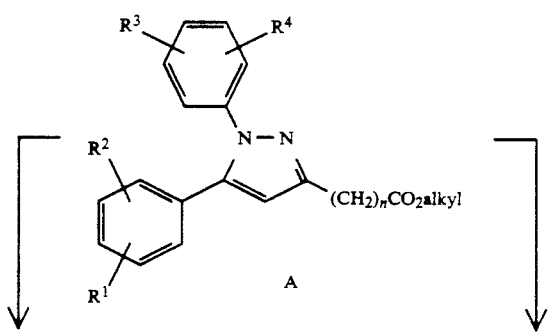

SCHEME 2 -continued

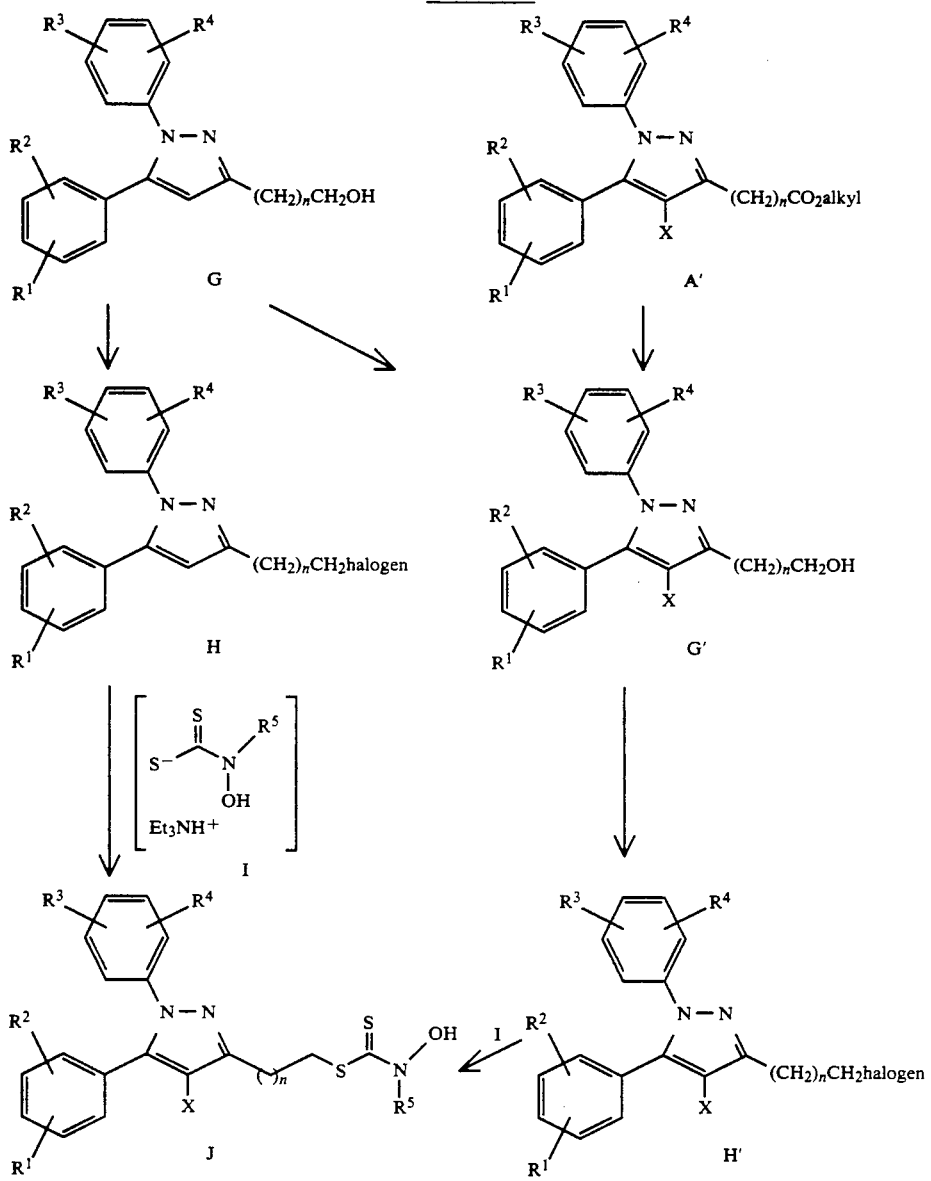

Preferred R¹ and R² include H, methyl, ethyl, isopropyl, trifluoromethyl, fluoro, chloro, bromo, methoxy, methylsulfinyl, ethylsulfinyl, methylsulfonyl, ethylsulfonyl, methylmercapto, ethylmercapto, and isopropylmercapto. In the most preferred compounds, R¹ and R² are a single substituent at the para-position.

Preferred R³ and R⁴ include H, methyl, ethyl, isopropyl, fluoro, chloro, bromo, methoxy, trifluoromethoxy, methylsulfinyl, ethylsulfinyl, methylsulfonyl, ethylsulfonyl, methylmercapto, ethylmercapto, and isopropylmercapto. In the most preferred compounds, R³ and R⁴ are a single substituent at the para-position.

Preferred R⁵ include H, methyl, ethyl, propyl, isopropyl, cyclopropyl, cyclobutyl, cyclopentyl, cyclohexyl, and phenyl.

The substituted pyrazole compounds of this invention are capable of inhibiting the lipoxygenase enzyme pathway and/or the cycloxygenase (prostaglandin synthetase) enzyme pathway to acheive the desired pharmacological effect. With an effective amount of the substituted pyrazole compounds dispersed in a pharmaceutical composition as an active ingredient, the pharmaceutical composition is introduced as a unit dose into an afflicted mammal.

The term "unit dosage" and its grammatical equivalent is used herein to refer to physically discrete units suitable as unitary dosages for human patients and other warm blooded mammals, each unit containing a predetermined effective, pharmacologic amount of the active ingredient calculated to produce the desired pharmacological effect in association with the required physiologically tolerable carrier, e.g., a diluent or a vehicle. The specifications for the novel unit dosage forms suitable for use herein are dictated by and are directly dependent on (a) the unique characteristics of the active ingredient, and (b) the limitations inherent in the art of compounding such an active ingredient for therapeutic use in humans and other mammals. Examples of suitable unit dosage forms in accord with this invention are tablets, capsules, pills, powder packets, granules, wafers and the like, segregated multiples of any of the foregoing, as well as liquid solutions and suspensions. The active ingredient is referred to herein as being dispersed in the carrier. The dispersion formed can be a simple admixture, a non-settling dispersion as in the case of certain emulsions, or as an ultimate dispersion, a true solution.

The amount of active ingredient that is administered in vivo depends on the age and weight of the mammal treated, the particular medical condition to be treated, the frequency of administration, and the route of administration. The dose range can be about 0.01 to about 500 milligrams per kilogram of body weight, more preferably about 0.1 to about 50 milligrams per kilogram of body weight and most preferably about 0.1 to about 25 milligram per kilogram of body weight. The human adult dose is in the range of about 10 to about 2000 milligrams daily, given as a single dose or in 3 or 4 divided doses. Veterinary dosages correspond to human dosages with the amounts administered being in proportion to the weight of the animal as compared to adult humans. When the compounds are employed to treat rheumatoid arthritis the dosage range can be about 0.01 to about 160 mg/kg. The preferred dosage range is from about 0.5 to about 80 mg/kg.

Physiologically tolerable carriers are well known in the art. Carriers may be divided into liquid and solid carriers.

Exemplary of liquid carriers are aqueous solutions that contain no materials in addition to the substituted pyrazole compound, or contain a buffer such as sodium phosphate at physiological pH value, saline and the like. Liquid compositions can also contain liquid phases in addition to and to the exclusion of water. Exemplary of such additional liquid phases are glycerin and vegetable oils such as cottonseed oil.

Exemplary solid carriers (diluents) include those materials usually used in the manufacture of pills or tablets, and include corn starch, lactose, dicalcium phosphate, thickeners such as tragacanth and methylcellulose U.S.P., finely divided $SiO_2$, polyvinylpyrrolidone, magnesium stearate and the like. Antioxidants such as methylparaben and propylparaben can be present in both solid and liquid compositions, as can sweeteners such as cane or beet sugar, sodium saccharin, sodium cyclamate, the dipeptide methyl ester sweetener sold under the trademark NUTRASWEET aspartame) by G. D. Searle Co.

The pharmaceutical composition can be administered orally, topically or by injection, by means well known in the art. In preferred practice, the composition is administered orally as a tablet, capsule or aqueous dispersion. The pharmaceutical composition is maintained within the mammal until the substituted pyrazole compound is cleared from the mammal's body by natural means such as excretion or metabolism.

Inasmuch as a pharmaceutical composition can be administered 3 to 4 times daily (per 24 hour period), the method of alleviating inflammation can include administering the pharmaceutical composition a plurality of times into the treated mammal over a time period of weeks, months and years. The pharmaceutical composition is administered a plurality of times to the mammal over a time period of thirty days, in preferred practice.

EXAMPLES

General Procedure for the Synthesis of N-Hydroxydithiocarbamates

The hydroxylamine hydrochloride (2 mole equivalents), and excess carbon disulfide are combined in a round bottom flask. Four equivalents of triethylamine are added at room temperature. After 10 minutes, dimethylformamide is added, followed by the chloromethylpyrazole (1 equivalent). The mixture is heated gently at 70° C. for as long as two hours. The mixture is cooled and partitioned between equal volumes of ether and water. The aqueous layer is extracted one time more with ether. The combined ether layers are dried over anhydrous sodium sulfate, filtered, and concentrated. The residue is crystallized from ether (or another suitable solvent), and/or is purified by chromatography on silica to obtain the product in a purified form.

By way of exemplification, in the $^1$HNMR (DMSO-$d_6$/TMS), this class of compounds characteristically shows singlets (delta, ppm from TMS) at the following chemical shifts: 2.3 ($R^1$=p-$CH_3$), 6.6 (X=H), 4.4 ($CH_2S$), and 3.7 ($R^5$=$CH_3$). The resonance for $R^3$=p-$OCH_3$ occurs at 3.75.

In the IR (KBr/cm$^{-1}$), characteristic absorptions occur at 1515, 1250, and 1015.

CI MS showed an M+1 peak for this series of compounds.

A specific procedure for the synthesis of 5-(4-chlorophenyl)-1-(4-methoxyphenyl)-3-pyrazolylmethyl-N-hydroxy-N-methyl dithiocarbamate

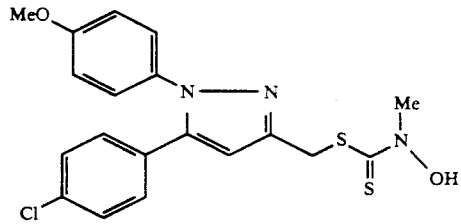

Methylhydroxylamine hydrochloride (1.10 g, 13 mmol) and $CS_2$ (10 mL, 170 mMol) were combined in a round bottom flask. Triethylamine (3.6 mL, 26 mmol) was added slowly. The reaction warmed slightly during the addition and turned yellow. DMF (10 mL) was added, followed by 3-chloromethyl-5-(4-chlorophenyl)-1-(4-methoxyphenyl)pyrazole (2.14 g, 6.4 mmol) in a single portion. The mixture was heated at 70° C. for two hours, after which time it was partitioned between 100 mL each of ether and water. The aqueous layer was extracted a second time with 100 mL of ether. The combined ether extracts were dried over anhydrous $Na_2SO_4$, filtered through celite, and concentrated. The crude residue was crystallized from ether to afford the product (1.70 g, 63%), mp 169°–169.5°, as a white solid.

$^1$H NMR (DMSO-$d_6$) delta, ppm: 3.69 (s, 3H, $NCH_3$), 3.77 (s, 3H, $OCH_3$), 4.39 (s, 2H, $CH_2S$), 6.62 (s, 1H, pyrazole 4H), 6.96 (d, 2H, J=9 Hz, aromatics), 7.41 (d, 2H, J=9 Hz, aromatics), 7.19 (overlapping d, 4-H, J=9 Hz, aromatics).

IR (KBr) cm$^1$ 2510, 1516, 1250, 1011.

CIMS (m/e) 420 (MH+), 331.

ANAL Calcd for $C_{19}H_{18}ClN_3O_2S_2$: C 54.34; H 4.32; N 10.01. Found: C 54.75; H 4.34; N 10.31.

The compounds of Table 1 were produced according to the general procedure given above.

TABLE 1

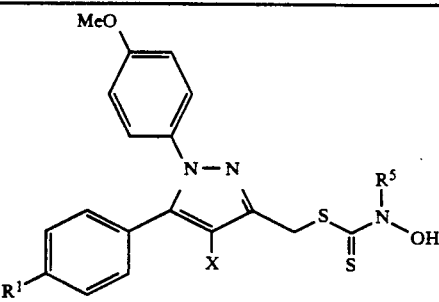

| CPD | $R^1$ | X | $R^5$ | mp °C. | C | H | N | Empirical Formula |
|---|---|---|---|---|---|---|---|---|
| 1-A | Cl | H | Me | 169–169.5 | 54.75 | 4.34 | 10.31 | $C_{19}H_{18}ClN_3O_2S_2$ |
| 1-B | Cl | H | i-Pr | — | 56.19 | 5.25 | 9.29 | $C_{21}H_{22}ClN_3O_2S_2$ |
| 1-C | Cl | Cl | Me | 158–160 | 49.09 | 3.66 | 8.96 | $C_{19}H_{17}Cl_2N_3O_2S_2 \cdot \frac{1}{4} H_2O$ |
| 1-D | Cl | Cl | i-Pr | — | 51.59 | 4.85 | 8.92 | $C_{21}H_{21}Cl_2N_3O_2S_2 \cdot \frac{1}{4} H_2O$ |
| 1-E | Cl | Br | i-Pr | — | 48.00 | 3.96 | 8.05 | $C_{21}H_{21}BrClN_3O_2S_2$ |
| 1-F | Me | H | Me | 159–160 | 60.42 | 5.32 | 10.35 | $C_{20}H_{21}N_3O_2S_2$ |
| 1-G | Me | H | i-Pr | 148–149 | 61.01 | 5.79 | 9.52 | $C_{22}H_{25}N_3O_2S_2 \cdot \frac{1}{4} H_2O$ |
| 1-H | Me | Cl | Me | 169–170 | 55.21 | 4.51 | 9.38 | $C_{20}H_{20}ClN_3O_2S_2$ |
| 1-I | Me | Cl | i-Pr | — | 55.76 | 5.20 | 8.49 | $C_{22}H_{24}ClN_3O_2S_2 \cdot \frac{1}{4} H_2O$ |
| 1-J | Me | Br | Me | 165–167 | 48.83 | 4.17 | 8.61 | $C_{20}H_{20}BrN_3O_2S_2 \cdot \frac{1}{4} H_2O$ |
| 1-K | Me | Br | i-Pr | 106–108 | 49.58 | 5.22 | 7.67 | $C_{22}H_{24}BrN_3O_2S_2 \cdot 3/2 H_2O$ |

Biological Results

Procedure I

Sheep seminal vesicle cyclooxygenase

Sheep seminal vesicle (SSV) cyclooxygenase (95% pure, prostaglandin endoperoxide synthase, EC 1.14.99.1 specific activity 24 units/mg protein) obtained as a lyophilized powder from Biomol (Plymouth Meeting, Pa.) was reconstituted at a concentration of 59 mg/mL in Hanks' Balanced Salt Solution (HBSS). The enzyme was divided into 200 μL aliquots, snap frozen with liquid $N_2$, and stored at $-70°$ C. unitl immediately prior to use. Measurements of CO activity were carried out in polypropylene tubes containing 495 μL of HBSS to which was added 5 μL of inhibitor or dimethylsulfoxide (DMSO; vehicle control) and 6 μL of SSV CO solution. The tubes were mixed on a vortex shaker, preincubated for 5 min at 37° C. prior to the initiation of the reaction. The reaction was started by the addition of [$^{14}$C]-arachidonic acid (1-$^{14}$C-AA, Amersham, Arlington Heights, Il) in 10 μL of methanol. Tubes were again vortexed and incubated in a water bath for 20 minutes after which the tubes were removed and the reaction stopped by acidification with the addition of 1 mL 2M formic acid. Lipophilic products were extracted with 3 mL chloroform and concentrated to dryness under $N_2$. Each pellet was reconstituted with 40 μL of chloroform and spotted on a Whatman Silicon thin-layer chromatography plate and developed in a chromatography tank containing A-9 solvent (11:5:2:1 V:V:V:V, ethyl acetate:trimethylpentane:acetic acid:double distilled-$H_2O$). Radioactive cyclooxygenase products (prostaglandin $D_2$, prostaglandin $E_2$, etc.) were measured using a Bioscan System 200 Imaging Scanner. Inhibition of enzyme activity was calculated by comparing the areas under the curve produced in the presence or absence of test compound.

Procedure II

RBL-1 cell 5-lipoxygenase and cyclooxygenase

Rat basophilic leukemia cells (RBL-1; $5 \times 10^7$ viable cells/mL) were disrupted by homogenization on ice (four 20 sec bursts) with a Brinkman polytron. Complete cell breakage was verified microscopically. The homogenate was then centrifuged at $10,000 \times g$ for 48 minutes at 4° C. The pellet was discarded and the supernatant was saved as the source of enzymes. The supernatant was pre-incubated for five minutes at 37° C. in the presence of 2 mM of $CaCl_2$ and compound or vehicle (1% DMSO). The conversion of AA into 5-LO products was initiated by adding 10 μL (50 μCi) of 1-$^{14}$C-AA to each tube and incubated at 37° C. for 20 minutes. The reaction was stopped by adjusting the pH of each sample to 3 to 3.5 with 2M formic acid. Samples were extracted with three volumes of chloroform to isolate the products of 5-LO formed during the reaction. Fractions were dried under nitrogen, then resuspended in 40 μL of chloroform and spotted onto silica gel HL plates. The plates were developed in A-9 solvent. The dried plates were analyzed using a Bioscan Imaging TLC scanner to determine the percentage of radiolabelled AA converted to 5-HETE in each sample.

Procedure III

The ability to inhibit 5-LO and CO in intact RBL-1 cells was also evaluated. RBL-1 cells were maintained in culture in minimal essential medium (Bio*Whittaker, Walkersville, MD), containing 12.5% fetal calf serum, 10 mg/mL streptomycin, 10 I.U./mL penicillin G, 50 mg/mL gentamycin and 2 mM L-glutamine (Bio*Whittaker, Walkersville, MD). Cells were collected by centrifugation, washed once in HBSS, and resuspended at a concentration of $1 \times 10^5$ cells/mL. Cells were incubated in the presence of vehicle or drug then centrifuged at $800 \times g$ for 10 minutes at 4° C. The supernatant was removed by aspiration and the cells were resuspended in 0.5 mL of HBSS. The reaction was started by the addition of 20 μg/mL of calcium ionophore A-23187 (mixed calcium and magnesium salts, Calbiochem, La Jolla CA) and allowed to proceed for 15 minutes, then stopped by plunging the tubes into a slush ice bath. The conversion of AA to 5-LO products was initiated by the addition of 10 μL (50 uCi) of 1-$^{14}$C-AA. Products were isolated by acidification and extraction, followed by thin layer chromatography analysis as described above. Radioactive areas corresponding to authentic 5-LO and CO products were quantitated by the Bioscan 2000 Imaging System.

Procedure IV

Ex Vivo eicosanoid synthesis in dog whole blood. Adult beagle or mongrel dogs (10–15 kg) of either sex were fasted overnight prior to the initiation of each experiment. The forelimb was clipped and swabbed with an alcohol prep (70% isopropanol). Blood was drawn by venipuncture into syringes containing lithium heparin (Starstead, Newton NC) immediately prior to administration of compound or vehicle and then at various intervals following dosing. The test compound was administered orally as a suspension in 0.5% methocel. At various times after dosing, blood samples were drawn and placed on an electric rocker platform to assure complete and continuous mixing. White blood cell (wbc) counts were performed using a Sysmex hematology analyzer. This was done in an effort to normalize the number of leukocytes to be stimulated with calcium ionophore. A 1.0 mL aliquot of whole blood was challenged with 50 μL of a $2.6 \times 10^{-5}$M solution of calcium ionophore A23187 (Calbiochem, La Jolla, CA) prepared in DMSO and diluted in HBSS. After a 15 minute incubation at 37° C., the reaction was stopped by placing the samples in an ice bath (4° C.) for 5 minutes and then centrifuged at 11,000×g for 5 minutes to separate the plasma fraction from blood cells. The plasma fraction was removed, diluted in an appropriate buffer, and analyzed for the presence of LTB$_4$ and prostaglandin F$_{2\alpha}$ or TxB$_2$ by standard RIA techniques. buffer, and analyzed for the presence of LTB$_4$ and prostaglandin F$_{2\alpha}$ or TxB$_2$ by standard RIA techniques.

In the following tables, the superscripts indicate the number of experiments and unless otherwise stated the concentration at which % inhibition is reported is 3 μM.

TABLE 2

| | PROC. I | | PROC. II | | | |
|---|---|---|---|---|---|---|
| | % INHIB | IC$_{50}$ (μM) | % INHIBITION | | IC$_{50}$ (μM) | |
| CPD | CO | CO | CO | 5-LO | CO | 5-LO |
| 1-A | — | — | 100 | 85 | — | — |
| 1-B | 39 | — | 100 | 100 | 8.07 | 0.57 |
| 1-C | 46 | — | 75 | 91 | — | — |
| 1-D | 31 | — | 0 | 70 | 1.67 | 0.07 |
| 1-E | 0 | — | 0 | 73 | 1.96 | 0.04 |
| 1-F | — | — | 100 | 83 | — | — |
| 1-G | 36 | — | 30 | 79 | 0.03 | 0.02 |
| 1-H | 39 | — | 95 | 91 | — | — |
| 1-I | 0 | — | 0 | 82 | — | — |
| 1-J | 36 | — | 52 | 83 | — | — |
| 1-K | 0 | — | 0 | 87 | — | — |

TABLE 3

| | PROC. III | | PROC. IV | | |
|---|---|---|---|---|---|
| | IC$_{50}$ (μM) | | DOSE | % INHIB/HOURS | |
| CPD | CO | 5-LO | (MPK) | CO | 5-LO |
| 1-A | 0.23 | 2.5 | — | — | — |
| 1-B | 1.4$^3$ | 7 | 1 | 77/2 | 36/2 |

TABLE 3-continued

| | PROC. III | | PROC. IV | | |
|---|---|---|---|---|---|
| | IC$_{50}$ (μM) | | DOSE | % INHIB/HOURS | |
| CPD | CO | 5-LO | (MPK) | CO | 5-LO |
| 1-C | 2.4 | 0.24 | — | — | — |
| 1-D | — | — | 5 | 32/24 | 2/6 |
| 1-E | 6.5 | 2.8 | 5 | 31/6 | 41/6 |
| 1-F | 0.06 | 2.4 | — | — | — |
| 1-G | 0.18 | 5.6 | — | — | — |
| 1-H | 1.6 | 0.67 | — | — | — |

What is claimed is:

1. An anti-inflammatory compound of the general formula:

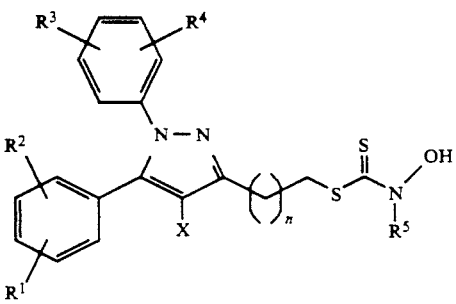

wherein,

R$^1$ and R$^2$ are independently selected from the group consisting of hydrogen, C$_{1-6}$ alkyl, C$_{1-6}$ perfluoroalkyl, halogen, C$_{1-6}$ alkoxy, C$_{1-6}$ alkylsulfinyl, C$_{1-6}$ alkylsulfonyl and C$_{1-6}$ alkylmercapto;

R$^3$ and R$^4$ are independently selected from the group consisting of hydrogen, C$_{1-6}$ alkyl, halogen, C$_{1-6}$ alkoxy, C$_{1-6}$ perfluoroalkoxy, C$_{1-6}$ alkylsulfinyl, C$_{1-6}$ alkylsulfonyl and C$_{1-6}$ alkylmercapto;

R$^5$ is selected from the group consisting of H, C$_{1-6}$ alkyl, C$_{1-6}$ cycloalkyl and phenyl;

n is 0, 1 or 2; and

X is selected from the group consisting of H, Cl, I and Br.

2. The compound of claim 1 wherein R$^1$ and R$^2$ are selected from the group consisting of H, methyl, ethyl, isopropyl, trifluoromethyl, fluoro, chloro, bromo, methoxy, methylsulfinyl, ethylsulfinyl, methylsulfonyl, ethylsulfonyl, methylmercapto, ethylmercapto and isopropylmercapto.

3. The compound of claim 1 wherein one of R$^1$ and R$^2$ is H and the other is at the para-position.

4. The compound of claim 1 wherein R$^3$ and R$^4$ include H, methyl, ethyl, isopropyl, fluoro, chloro, bromo, methoxy, trifluoromethoxy, methylsulfinyl, ethylsulfinyl, methylsulfonyl, ethylsulfonyl, methylmercapto, ethylmercapto, and isopropylmercapto.

5. The compound of claim 1 wherein one of R$^3$ and R$^4$ is H and the other is at the para-position.

6. The compound of claim 1 wherein R$^5$ include H, methyl, ethyl, propyl, isopropyl, cyclopropyl, cyclobutyl, cyclopentyl, cyclohexyl, and phenyl.

7. The compound of claim 1 having the general formula:

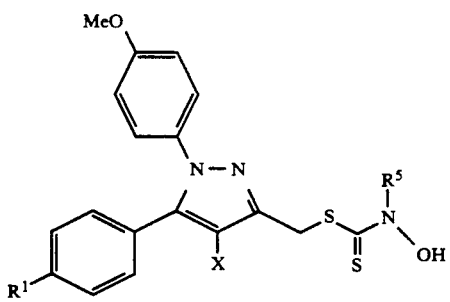

wherein $R^1$, X and $R^5$ are selected in concert from the group consisting of:

| $R^1$ | X | $R^5$ |
|---|---|---|
| Cl | H | Me, |
| Cl | H | i-Pr, |
| Cl | Cl | Me, |
| Cl | Cl | i-Pr, |
| Cl | Br | i-Pr, |
| Me | H | Me, |
| Me | H | i-Pr, |
| Me | Cl | Me, |

-continued

| $R^1$ | X | $R^5$ |
|---|---|---|
| Me | Cl | i-Pr, |
| Me | Br | Me, and |
| Me | Br | i-Pr. |

8. A method to alleviate inflammation in a mammal exhibiting an inflammatory condition, the method comprising administering to the mammal an effective amount of a pharmaceutical composition containing a unit dose of the compound of claim 1 dispersed in a pharmaceutically acceptable carrier.

9. The method of claim 8 wherein said inflammation is the result of a disease state selected from the group consisting of asthma, arthritis, hypersensitivity, myocardial ischemia, psoriasis, dermatitis and inflammatory bowel syndrome.

10. A pharmaceutical composition for administration to a mammal to alleviate inflammation comprising a unit dose of the compound of claim 1 dispersed in a pharmaceutically acceptable carrier.

11. The pharmaceutical composition of claim 10 wherein said compound dispersed in said pharmaceutically acceptable carrier is capable of inhibiting both the cyclooxygenase and lipoxygenase pathways in the amount present in the composition upon administration to a mammal.

* * * * *